US006808521B1

(12) United States Patent
McMichael

(10) Patent No.: US 6,808,521 B1
(45) Date of Patent: Oct. 26, 2004

(54) ENTERAL FEEDING ADAPTER

(75) Inventor: Donald J. McMichael, South Jordan, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 129 days.

(21) Appl. No.: 09/660,665

(22) Filed: Sep. 13, 2000

Related U.S. Application Data

(60) Provisional application No. 60/166,202, filed on Nov. 18, 1999.

(51) Int. Cl.[7] ........................ A61M 25/00; A61M 25/16; A61M 25/18; F16L 55/00

(52) U.S. Cl. .................. 604/533; 285/148.23; 604/175; 604/523; 604/534

(58) Field of Search ................................ 604/533–256, 604/175, 903, 77, 167.04–167.01, 167.11, 248, 264, 167.06, 905; 283/148.23, 148.24, 8; 138/116

(56) References Cited

U.S. PATENT DOCUMENTS 4,666,433 A 5/1987 Parks
4,685,901 A 8/1987 Parks
4,701,163 A 10/1987 Parks
5,234,417 A 8/1993 Parks et al.
5,250,040 A 10/1993 Parks et al.
5,267,983 A * 12/1993 Oilschlager et al. ... 285/148.24
5,399,173 A * 3/1995 Parks et al. ................. 604/533
5,458,583 A 10/1995 McNeely et al.
5,988,700 A * 11/1999 Prichard ................ 285/148.23
5,997,503 A 12/1999 Willis et al.
5,997,546 A 12/1999 Foster et al.

* cited by examiner

*Primary Examiner*—Brian L. Casler
*Assistant Examiner*—Roz Maiorino
(74) *Attorney, Agent, or Firm*—Dority & Manning, P.A.

(57) ABSTRACT

An enteral feeding adapter is disclosed for use with a medical feeding device to deliver substances into a patient, the enteral feeding adapter being suitable for use with a plurality of infusion sets having distal connectors of differing dimensions. The enteral feeding adapter includes an adapter body containing at least a first port configured for receiving a distal connector of an infusion set, the first port having at least one arcuate sidewall for frictionally engaging the distal connector to sealingly secure the distal connector to the adapter body. The enteral feeding adapter also includes a tube extending between the first port and the medical device for transmitting substances that pass through the first port to the medical device. Related methods are also disclosed.

23 Claims, 10 Drawing Sheets

ENTERAL FEEDING ADAPTER

This application claims the benefit of Provisional application Ser. No. 60/166,202, filed Nov. 18, 1999.

This application claims priority under 35 U.S.C. § 119(e) to prior co-pending Provisional Application Ser. No. 60/166,202, filed Nov. 18, 1999, and such prior application is incorporated by reference herein.

BACKGROUND OF THE INVENTION

The present invention relates generally to enteral feeding devices, and more particularly to an enteral feeding adapter which may be used with infusion sets of various sizes.

It is a known medical procedure to catheterize a body in order to provide nutritional solutions directly into the stomach or intestines of a patient. A stoma is formed in the stomach or intestinal wall and a catheter is placed through the stoma. Feeding solutions can be injected through a catheter inserted in the stoma to provide nutrients directly to the stomach or intestines (known as enteral feeding).

To ensure that the catheter is maintained in the proper position, it is common to use a balloon disposed near the distal (patient) end of the catheter shaft. Inflating the balloon causes the balloon to contact the anatomical structure (i.e., a duct or stomach wall) and thereby prevent the catheter from moving out of the proper position. Such balloon catheter devices may include a "low-profile" head at the proximal end of the catheter shaft. The head, which also helps hold the balloon catheter in place, includes an opening for receiving the feeding solution and a one-way valve for preventing fluids from passing out of the patient via the catheter. U.S. Pat. No. 5,997,503 and 5,997,546, both owned by Applicants' Assignee and incorporated by reference herein for all purposes, disclose examples of low-profile balloon catheters suitable for enteral feeding.

The balloon catheters of the cited patents are configured to have a low profile above the user's skin so that the catheters do not significantly interfere with the patient's other activities. Because feeding solutions must be fed through the relatively small head of the balloon catheter located atop the patient's skin, an enteral feeding adapter is often used to transfer the solutions from a source to the catheter.

Such adapters often include an elongate feeding tube having connecting elements on each end of the tube. On the distal end of the tube, one of the connecting elements engages the head of the balloon catheter to place the tube in communication with the catheter. The proximal end of the tube typically includes another connecting element in the form of an adapter body for receiving the distal end of an infusion set and also possibly a syringe. The infusion set, in turn, may be connected to an enteral feeding pump, a drip chamber, or any other mechanism for providing a feeding solution.

One problem with available enteral feeding adapters is that the adapter bodies are typically configured specifically for use with a particular infusion set of a given diameter and configuration. Most of the commercially available infusion sets, however, are not of a standardized size or configuration. For example, infusion sets marketed by various companies have widely different distal end configurations. Some have substantially cylindrical surfaces at the infusion set distal end, and some have substantially frustoconical surfaces at this location. Additionally, although infusion sets and mating enteral feeding adapters are made in varying sizes, only a very limited range exists where infusion sets and adapters of differing sizes might work together. For example, if a portion of the distal end of an infusion set is configured to be received in an adapter having a cross-sectional diameter of 0.22 inches, the distal end will likely not work in an adapter with a cross-sectional diameter of 0.24 inches. While the infusion set distal end would be received by the adapter body, the engagement would be so loose that the distal end could easily be pulled from the adapter.

Thus, infusion sets and the adapters are generally not interchangeable. To provide an enteral feeding adapter for a patient, the infusion set and the enteral feeding adapter typically must be matched. This situation can lead to inventory and supply problems, added cost and complexity, etc. The situation can be compounded greatly where the enteral feeding adapter distal end does not work with all balloon catheters.

Frustoconically shaped feeding ports, although they may allow infusion sets of differing sizes to be inserted, inherently may provide only limited contact between the exterior of the distal end of the infusion set and the frustoconical port's wall. Thus, the distal end of the infusion set may be easily pulled from the feeding port.

Thus, there is a need for an improved enteral feeding adapter which can be used with a wide variety of infusion sets while inhibiting inadvertent removal of the distal end of the infusion set from the feeding port of the adapter body.

SUMMARY OF THE INVENTION

Objects and advantages of the invention will be set forth in part in the following description, or may be apparent from the description, or may be learned through practice of the invention.

It should be noted that any given range presented herein is intended to include any and all lesser included ranges. For example, a range of from 45–90 would also include 50–90, 45–80, 46–89, and the like.

According to the invention, an adapter is provided for use with an enteral feeding device for delivering substances into a patient. The enteral feeding adapter is suitable for use with a plurality of infusion sets having distal connectors of differing dimensions. The enteral feeding adapter includes an adapter body containing at least a first port configured for receiving a distal connector of an infusion set, the first port having at least one arcuate sidewall for frictionally engaging the distal connector to sealingly secure the distal connector to the adapter body. The arcuate sidewall may have various radii of curvatures, for example between about 0.18 inches to about 0.55 inches. The enteral feeding adapter also includes a tube extending between the first port and the medical device for transmitting substances that pass through the first port to the medical device.

A second port may also be defined in the adapter for delivering medicine to the patient, for example by a syringe.

The at least one arcuate sidewall may define a proximal portion of the first port, and the first port may further include a second arcuate sidewall, which may be located distally the first arcuate sidewall. If so, the first arcuate sidewall may have a radius of curvature greater than that of the second arcuate sidewall. For example, the first arcuate sidewall may have a radius of curvature of between 0.45 and 0.55 inches and the second arcuate sidewall may have a radius of curvature between 0.22 and 0.24 inches.

The first port may also include a third arcuate sidewall distal of the second arcuate sidewall. If so, the first arcuate sidewall may have a radius of curvature of between 0.45 and 0.55 inches, the second arcuate sidewall may have a radius of curvature of between 0.22 and 0.24 inches, and the third arcuate sidewall may have a radius of curvature of between 0.18 and 0.22 inches.

The first arcuate sidewall may have a varying diameter between 0.330 and 0.220 inches, the second arcuate sidewall may have a varying diameter between 0.220 and 0.153 inches, and the third arcuate sidewall may have a varying diameter between 0.153 and 0.127 inches.

In accordance with another aspect of the invention, an enteral feeding adapter is provided and configured for receiving the distal end of an infusion set for delivering substances into a patient. The enteral feeding adapter includes an adapter body having a first port, the first port having at least a cylindrical first section and a second section defined by a first arcuate sidewall disposed distally of the first section, the first arcuate sidewall being configured to frictionally engage the distal end of the infusion set. The adapter also includes a tube extending between the adapter body and the medical device for transmitting the substances from the infusion set to the medical device and thereafter into the patient.

The present invention also includes the methods of utilizing the enteral feeding adapter described herein.

DETAILED DESCRIPTION

Embodiments of the invention will now be described in detail with reference to examples shown in the figures. Each example is provided by way of explaining the invention, and not as a limitation of the invention. Various modifications and variations can be made in the invention without departing from the scope and spirit of the invention. For example, features illustrated or described with respect to one embodiment may be used in another embodiment to yield still a further embodiment.

Figure 1:
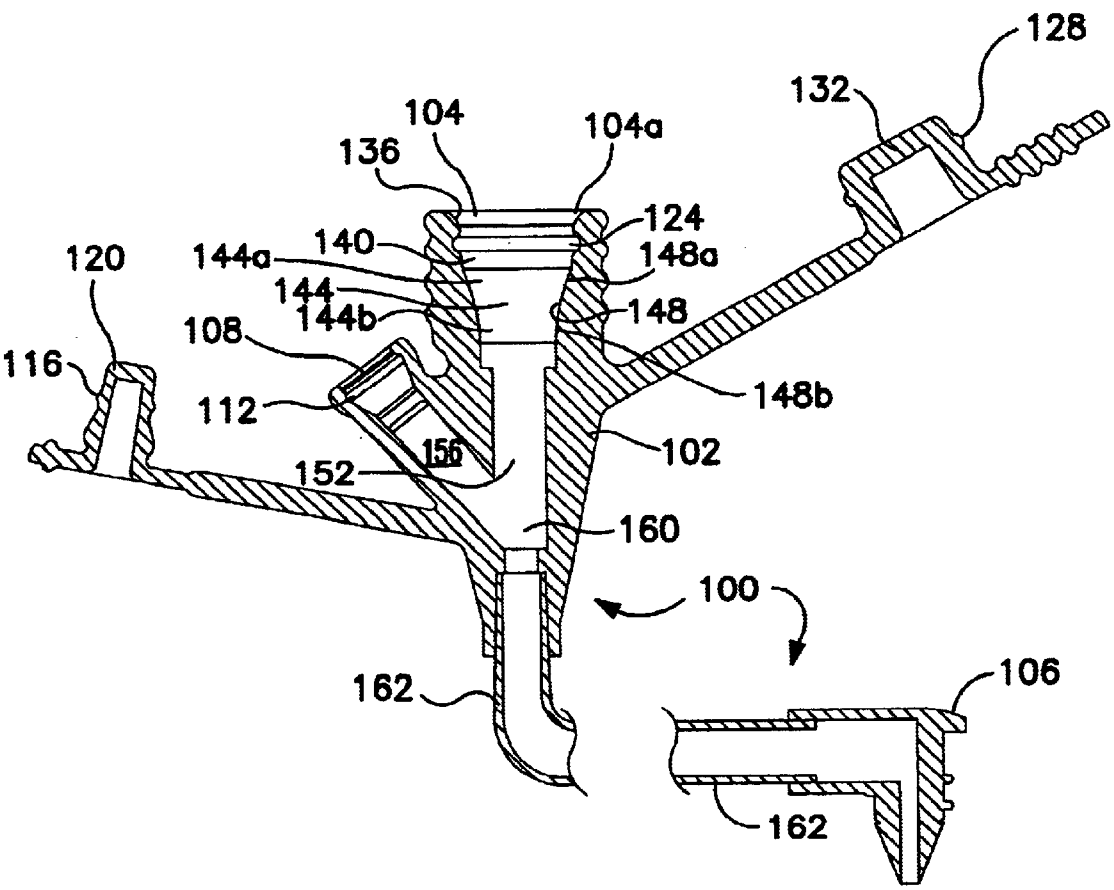
FIG. 1 shows a cross-sectional view of an enteral feeding adapter made in accordance with the present invention.

Turning now to FIG. 1, an enteral feeding adapter 100 according to the invention is shown. The adapter 100 includes a proximal adapter body 102, a distal end connector 106, and an adapter tube 162 extending therebetween. The adapter body 102 has a first port 104 and a second port 108 is a feed port configured for receipt of the distal end of an infusion set and is discussed in detail below. The port 108 is a medication port configured for the injection of medication therethrough and is sized to receive the distal end of a syringe. One or more grooves 112 are formed in the second port 108 to receive the nub 116 of a cap 120 so as to securely close the medication port 108 when it is not in use.

The feed port 104 may also include a groove 124 to receive the nub 128 of a cap 132. The groove 124 is most often disposed adjacent the proximal end 104*a* of the feed port 104. A tapered entry 136 can also be provided at the proximal end 104*a* of the port 104.

As shown in FIG. 1, the first port 104 has a channel formed therein which has three general sections. A first proximal section 140 is generally cylindrical with a constant diameter, for example a diameter of approximately 0.330 inches. The first proximal section 140 is designed to receive the distal end of an infusion set (not shown in FIG. 1). Typically, the first proximal section 140 will have a diameter slightly larger than that of the infusion set so that the distal end of the infusion set can be advanced through the first proximal section. However, an infusion set which has a portion which is substantially the same outer diameter as the inner diameter of the first proximal section 140 can be nested in the first proximal section 140 if desired.

Disposed adjacent the first proximal section 140 is a second proximal section 144 having an arcuate (convex) sidewall 148 which tapers inwardly and distally. (As used herein, an "arcuate sidewall" refers to the sidewall being arcuate from a proximal end to a distal end and not to an annular sidewall defining a cylinder.)

It should be appreciated that the adapter 100 according to the invention is not limited to particular dimension or size. By way of example, the arcuate sidewall 148 may have a radius of curvature of about 0.5 inches. For the presently available infusion sets, a radius of curvature of about 0.45 to about 0.55 inches, about 0.22 to about 0.24 inches, or about 0.18 to about 0.22 inches is preferred depending on the diameter of the second proximal section 144.

Disposed distally from the second proximal section 144 is a third proximal section 152 defining a generally straight channel which extends distally until it joins the channel 156 extending through the second port 108. From that point, a single distal channel 160 is formed for directing enteral feeding solutions and medication to the patient through the adapter tube 162 and the distal end 106 of the adapter 100.

Figure 2:
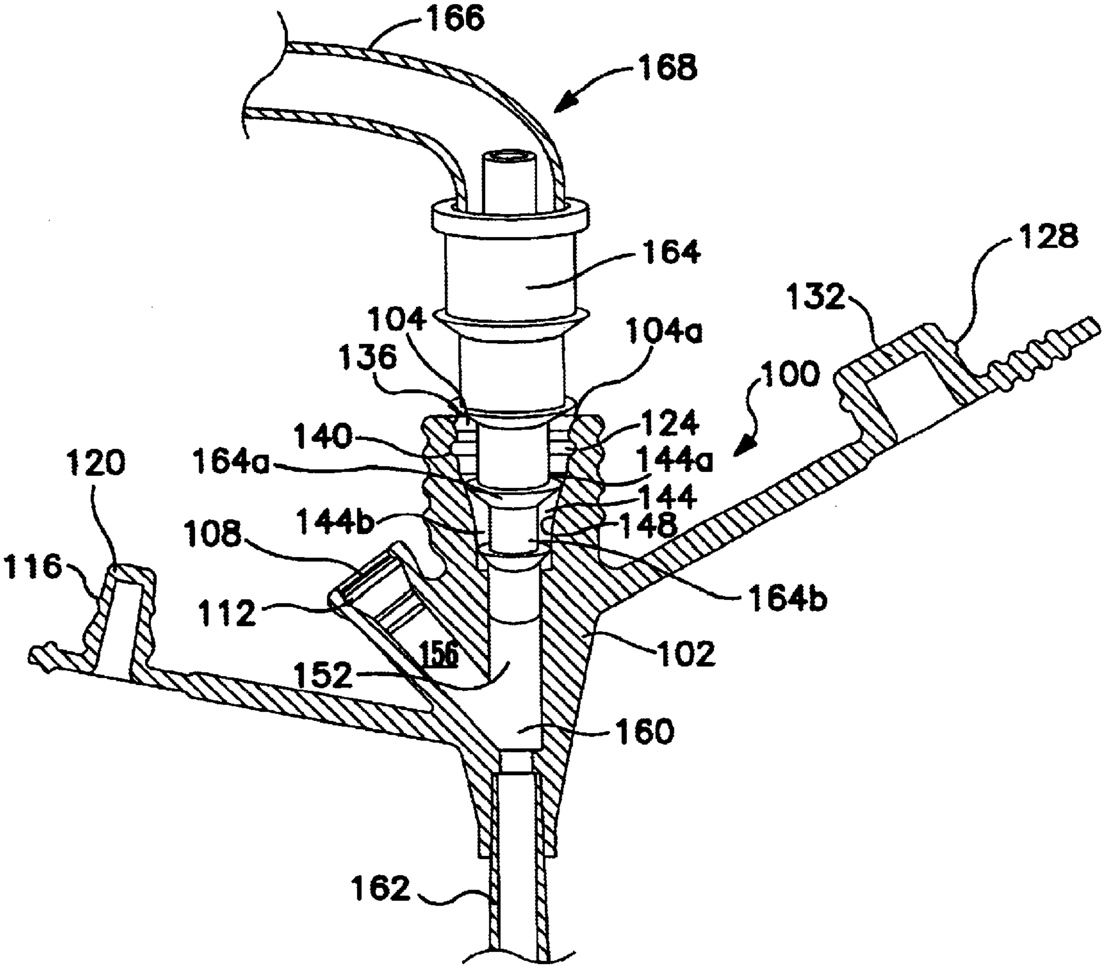
FIG. 2 shows a cross-sectional view of the enteral feeding adapter body of FIG. 1 with the distal end of an infusion set disposed therein.

In FIG. 2, a distal end 164 and tube 166 of an infusion set 168 is shown mated with the adapter body 102. The distal end of the infusion set would be carefully sized to nest in the feed port 104. However, the arcuate sidewall 148 of feed port 104 accommodates a relatively wide range of outer diameters which can be held in the feed port 104.

The arcuate sidewall 148 forms a channel having a varying diameter. The largest diameter occurs at the top or proximal end 144*a* of the second proximal section 144 and may be, for example, approximately 0.330 inches. At an opposing distal end 144*b* of the second proximal section 144, the diameter may be, for example, only about 0.220 inches.

Thus, the distal end 164 of virtually any infusion set having an outer diameter of any size between 0.330 inches and 0.220 inches will engage the arcuate sidewall 148 and secure the infusion set. The exact point of engagement will depend upon the size of the outer diameter of the infusion set 164; the larger the outer the diameter, the closer to the proximal end 144*a* the engagement occurs. Thus, as shown in FIG. 2, the distal end 164 of an infusion set 168 has stepped (and ringed) segments, one outer ring 164*a* of which has an outer diameter of approximately 0.300 inches. The ring 164*a* is held secure adjacent the proximal end 144*a* of the arcuate section 144 defined by sidewall 148.

To further facilitate engagement, the adapter body 102 is preferably formed of flexible pvc or some other slightly deformable substance to maximize the area of the sidewall 148 which engages the distal end 164 of the infusion set 168. In addition to the above, depending on the configuration of the steps of the distal end 164, the arcuate sidewall 148 can actually engage an additional step, such as ring 164*b* to provide an even more secure hold of the distal end.

Figure 3:
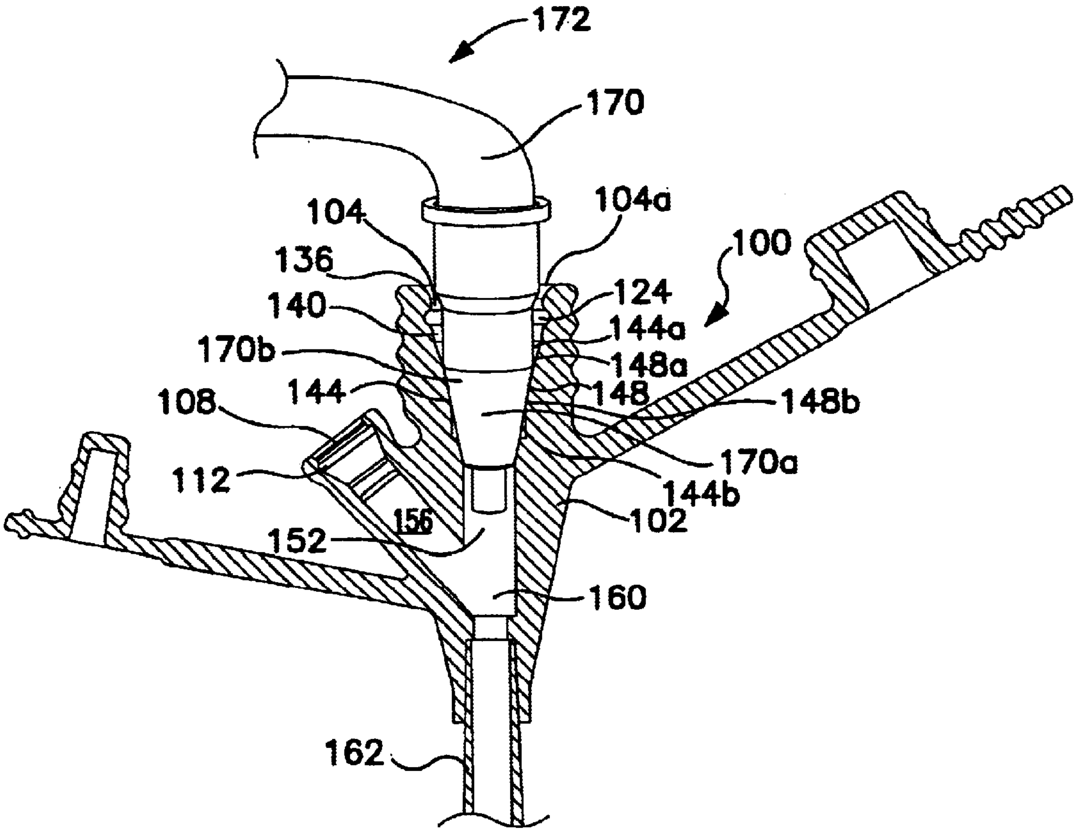
FIG. 3 shows a cross-sectional view of the enteral feeding adapter body of FIG. 1 with the distal end of an infusion set having a different outer diameter than that shown in FIG. 2.

In contrast, FIG. 3 shows an alternate infusion set 172 which has a distal end 170 with a frustoconical step 170*a*. The distal end 170 of the infusion set is advanced until the proximal end 170*b* of the step 170*a* is only a short distance from the distal end 148*b* of the arcuate sidewall 148. The step 170*a* then engages the arcuate sidewall 148 as shown in FIG. 3. An infusion set having a step or ring with an outer diameter between that of the proximal and distal ends 148*a* and 148*b* of arcuate wall 148 would advance to a position between the proximal and distal ends of the arcuate wall. Thus, those skilled in the art will appreciate that a wider range of infusion sets can be used with the feed port 104 of the adapter 100 than with prior art configurations. Further, one significant advantage which the arcuate sidewall 148 provides is that the diameter at the point at which the infusion set distal end engages the sidewall changes gradually. This provides a greater surface area for forming the friction fit necessary to securely hold the distal end, especially for distal end configurations such as that shown in FIG. 3.

Figure 4:
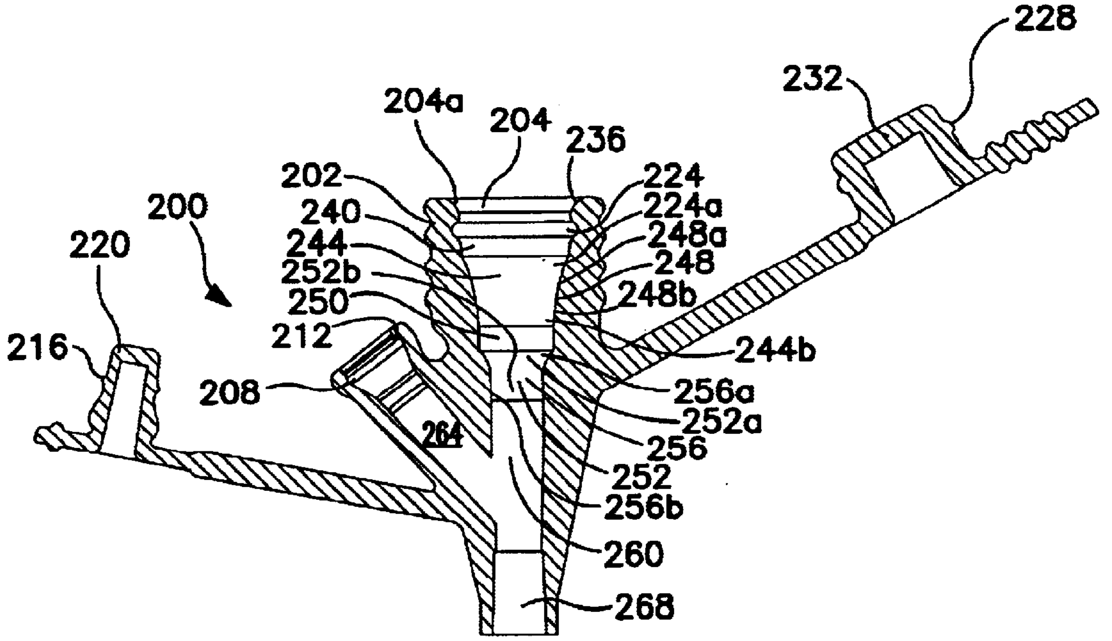
FIG. 4 shows a cross-sectional view of another embodiment of an enteral feeding adapter body made in accordance with the present invention.

FIG. 4 illustrates an embodiment having two arcuate sidewall portions with different diameters. This configuration provides even further improved compatibility with variously sized infusion sets. An enteral feeding adapter 200 includes an adapter body 202 made of flexible pvc or some other similar medical grade material. For simplicity's sake, no adapter tube or distal end are shown in FIG. 4., but it should be understood that the elements shown in FIGS. 1–3 could be suitably utilized with the adapter body 202 of FIG. 4.

The adapter body 202 includes a first feed port 204 configured for receipt of the distal end of an infusion set and a second medication port 208 provided for the injection of medication. The second port 208 will typically have structures similar to the second port of FIG. 1 and therefore will not be discussed in detail.

The first port 204 may include a groove 224 to receive the nub 228 of a cap 232.

The groove 224 is typically disposed adjacent the proximal end 204*a* of the port 204. A tapered entry 236 can also be provided at the proximal end 204*a* of the port 204.

As shown in FIG. 4, the first port 204 has four general sections. A first proximal section 240 is sized to receive the distal end of an infusion set and may be, for example, approximately 0.330 inches in diameter. Typically, the first proximal section 240 will be slightly larger than the distal end of the feeding set. However, an infusion set could have substantially the same outer diameter as the diameter of the first proximal section 240 and thereby nest snugly in the first proximal section 240.

The adapter body 202 also forms a second proximal section 244 disposed distally from the first proximal section 240. The second proximal section 244 is defined by an arcuate sidewall 248 so that a proximal end 244*a* of the second proximal section 244 has a larger diameter than a distal end 244*b* of the second proximal section. Optionally, the second proximal section 244 may have a linear portion at either end. For example, a linear portion 250 having a cylindrical shape is disposed at the distal end 244*b* of the second proximal section 244 for spacing purposes.

As with the previous embodiment, a preferred radius of curvature for the arcuate sidewall 248 is approximately 0.500 inches. This gradual curve provides sufficient surface area to securely, frictionally engage the distal end of an infusion set.

A third proximal section 252 of the feed port 204 is disposed adjacent to and distally from the second proximal section 244. The third proximal section 252 preferably includes a second arcuate sidewall 256. As with the sidewall 248 of the second proximal section 244, the sidewall 256 is arcuate extending from a proximal end 256*a* to a distal end 256*b*, but may include a linear portion (not shown) adjacent the distal end 256*b*. The proximal end 256*a* may have an inner diameter of approximately 0.220 inches and the distal end 256*b* may have an inner diameter of approximately 0.153 inches.

The radius of curvature of the second arcuate sidewall 256 is less than that of the first arcuate sidewall 248, for example between about 0.22 inches and 0.24 inches. More particularly, the radius of curvature may be about 0.231 inches.

The second arcuate sidewall 256 is advantageous in that it enables the adapter body 202 to receive and secure the distal end of an infusion set which has an outer diameter which would not be secured by the first arcuate sidewall 248. For example, with the diameters stated above, the first arcuate sidewall 248 will receive and secure the distal end of an infusion set having an outer diameter between 0.330 inches and 0.220 inches, and the second arcuate sidewall will receive and secure a distal end having a diameter between 0.22 inches and 0.153 inches. Thus, the adapter body 202 provides a range between about 0.153 inches to 0.330 inches.

Disposed distally of the third proximal section 252 is a fourth proximal section 260 defining a generally linear channel which extends distally until it joins the distal channel 264 extending through the second port 208. From that point, a single distal channel 268 is formed for directing enteral feeding solutions and medication to the patient.

Figure 5:
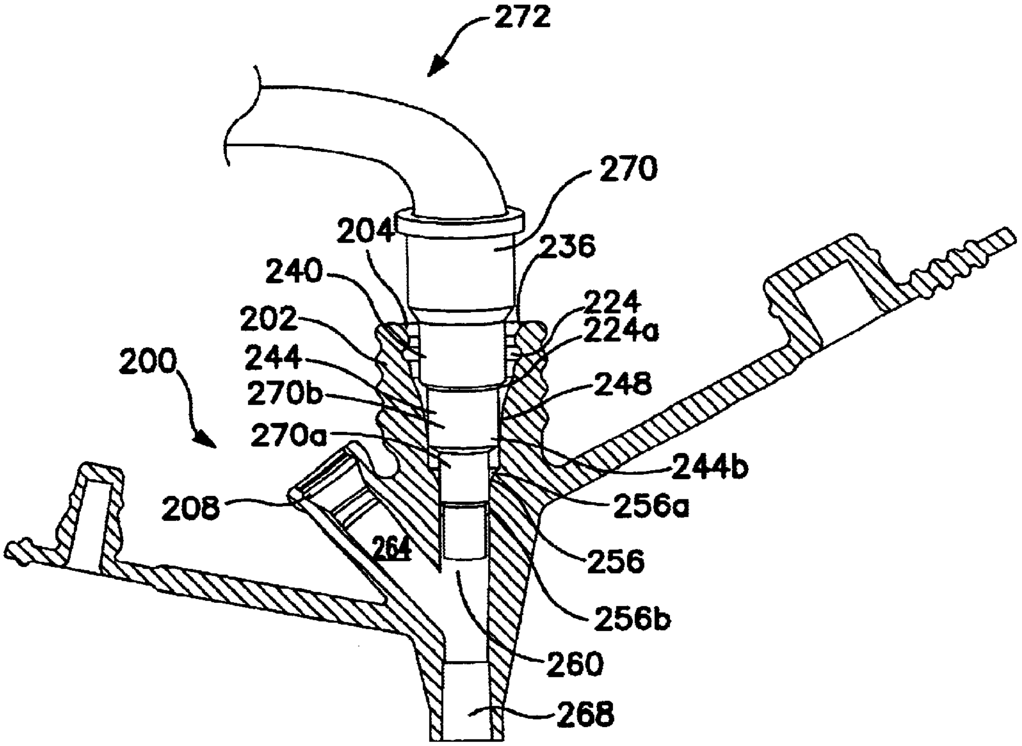
FIG. 5 shows a cross-sectional view of the enteral feeding adapter body of FIG. 4 with the distal end of an infusion set disposed therein.

FIG. 5 shows the adapter body 202 shown in FIG. 4 mated with the distal portions of end 270 of an infusion set 272. The distal end 270 is advanced through the first and second proximal sections 240 and 244, and into engagement with the second arcuate sidewall 256 which forms the third proximal section 252 of the feed port 204. The distal end 270 of the infusion set has a step 270*a* with an outer diameter of approximately 0.16 inches. Thus, the step 270*a* of the distal end 270 engages the arcuate sidewall 256 near the distal end 256*b*. If the step 270*a* of the distal end 270 were larger (i.e. 0.20 inches) it would engage the arcuate sidewall 256 adjacent the proximal end 256*a*.

Also shown in FIG. 5 is a more proximal step 270*b* of the distal end 270 having a diameter between 0.220 inches and 0.330 inches. The proximal step 270*b* engages the first arcuate sidewall 248 to provide an enhanced engagement between the distal end 270 and the adapter body 202.

Figure 6:
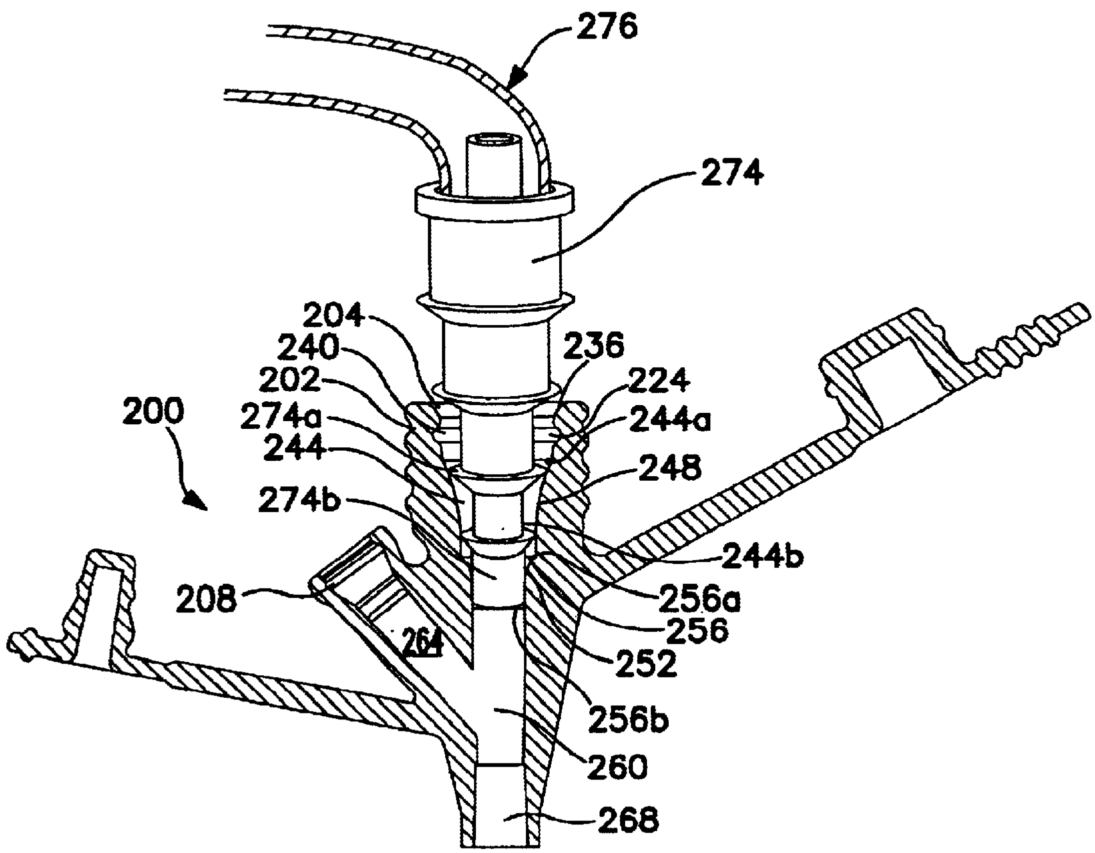
FIG. 6 shows a cross-sectional view of the enteral feeding adapter body of FIG. 4 with the distal end of an infusion set having a different outer diameter than that of FIG. 5.

FIG. 6 shows the adapter body 202 of FIGS. 4 and 5 with an alternate distal end 274 of an infusion set 276. The distal end 274 has two steps 274*a* and 274*b* which respectively engage the first and second arcuate sidewalls 248 and 256. (Step 274*a* comprises a ring as shown). Thus, the adapter body 202, having two arcuate surfaces can provide two (substantially circular) points of sealing engagement with a distal end of certain infusion sets. However, while a double engagement is desirable, it is not necessary to ensure a secure hold of the distal end of an infusion set. Having a single step firmly engage one of the arcuate sidewalls 248 or 256 is adequate.

Thus, the dual arcuate sidewall configuration of the adapter body 202 shown in FIGS. 4 through 6 provides a marked improvement over the prior art because of the broad range of infusion sets with which it can be used. Those skilled in the art will appreciate that modifications can be made so that the adapter body 202 could receive other sizes if desired.

Figure 7:
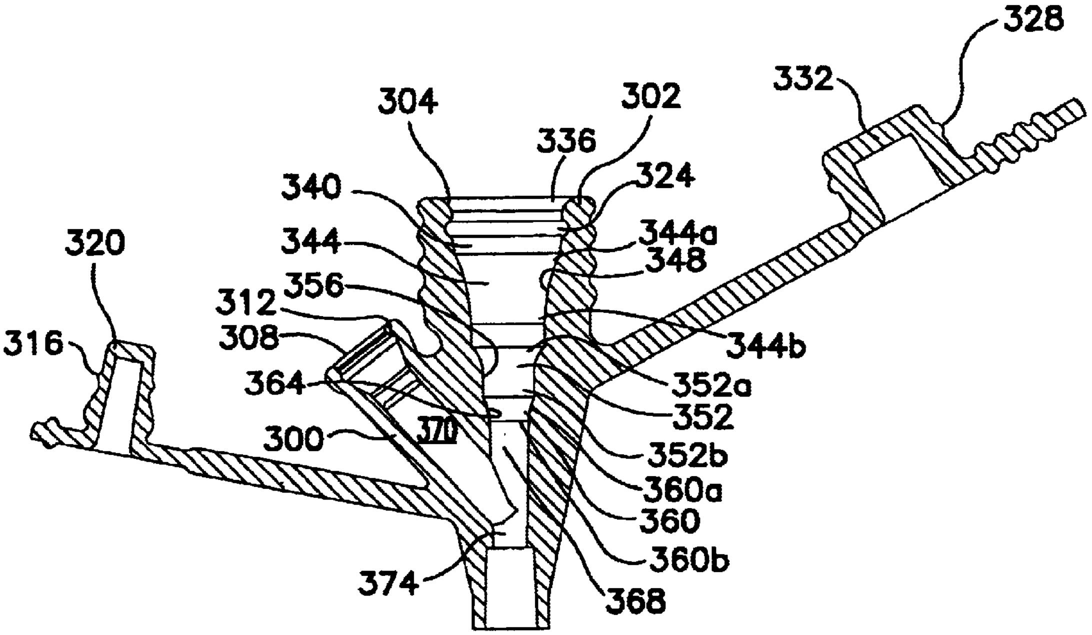
FIG. 7 shows a cross-sectional view of yet another embodiment of an enteral feeding adapter body made in accordance with the present invention.

FIG. 7 shows a cross-sectional view of another embodiment of an adapter body 302. The adapter body 302 defines a first feed port 304 and a second medication port 308.

The medication port 308 has one or more grooves 312 formed therein to receive the nub 316 of a cap 320 which is attached to the adapter body 302. The cap 320 enables the user to securely close the medication port 308 when it is not in use.

The feed port 304 is also provided with a groove 324 to receive the nub 328 of a cap 332. A tapered entry 336 can also be provided in the port 304.

The feed port 304 includes five proximal sections which facilitate the retention of the distal end of an infusion set. The first proximal section 340 is disposed adjacent the proximal end 304*a* of feed port 304 and forms a generally cylindrical void having a diameter of, for example, approximately 0.330 inches.

Disposed distally from but adjacent to the first proximal section 340 is a second proximal section 344. The sidewall 348 which defines the second proximal section 344 tapers inwardly between the proximal end 344*a* and the distal end 344*b* of the second proximal section. The arcuate taper of the sidewall 348 has a radius of curvature, for example between about 0.450 and 0.550 inches, and particularly 0.500 inches. Thus, while the proximal end 344*a* of the second proximal section 344 has an inner diameter of 0.330 inches, the inner diameter decreases to approximately 0.220 by the distal end 344*b*. Such a configuration allows the second proximal section 344 to secure infusion sets having outer diameters from between about 0.220 to 0.330 inches. A cylindrical portion 350 may be disposed distally to second proximal section 344.

Disposed distally from the second proximal section 344 is a third proximal section 352. At a proximal end 352*a*, the third proximal section 352 as a diameter of about 0.220 inches. At an opposing distal end 352*b*, the diameter of the third proximal section 352 is reduced to 0.153 inches. The reduction is preferably accomplished by a second arcuate sidewall 356 having a radius of curvature between about 0.220 inches and 0.240 inches, and more particularly 0.231. Thus, the distal end of an infusion set with an outer diameter between about 0.220 inches and 0.153 inches will be securely held in the third proximal section 352.

The feed port 304 also includes a fourth proximal section 360. The proximal end 360*a* of the fourth proximal section 360 is disposed adjacent the distal end 352*b* of the third proximal section 352 and has a diameter of approximately 0.153 inches. The fourth proximal section 360 has an arcuate sidewall 364 so that the section tapers inwardly toward the distal end 360*b*. At the distal end 360*b*, the sidewall 364 has a diameter which is approximately 0.127 inches. The radius of curvature of the sidewall 364 may be between about 0.18 and 0.22 inches, and more particularly 0.200 inches.

Disposed distally from the fourth proximal section 360 is a fifth proximal section 368. The fifth proximal section 368 forms a generally cylindrical channel which extends distally until it joins a channel 370 extending through the second port 308. From that point, a single distal channel 374 is formed for directing enteral feeding solutions and medication to the patient.

As with the two previous embodiments, the configuration shown in FIG. 7 provides a significant advantage over the prior art in that an infusion set having an outer diameter of between 0.127 inches and 0.330 inches may be snugly nested in the feed port 304. This is in contrast to the prior art embodiments which typically provide a range of only a few hundredths of an inch.

Figure 8:
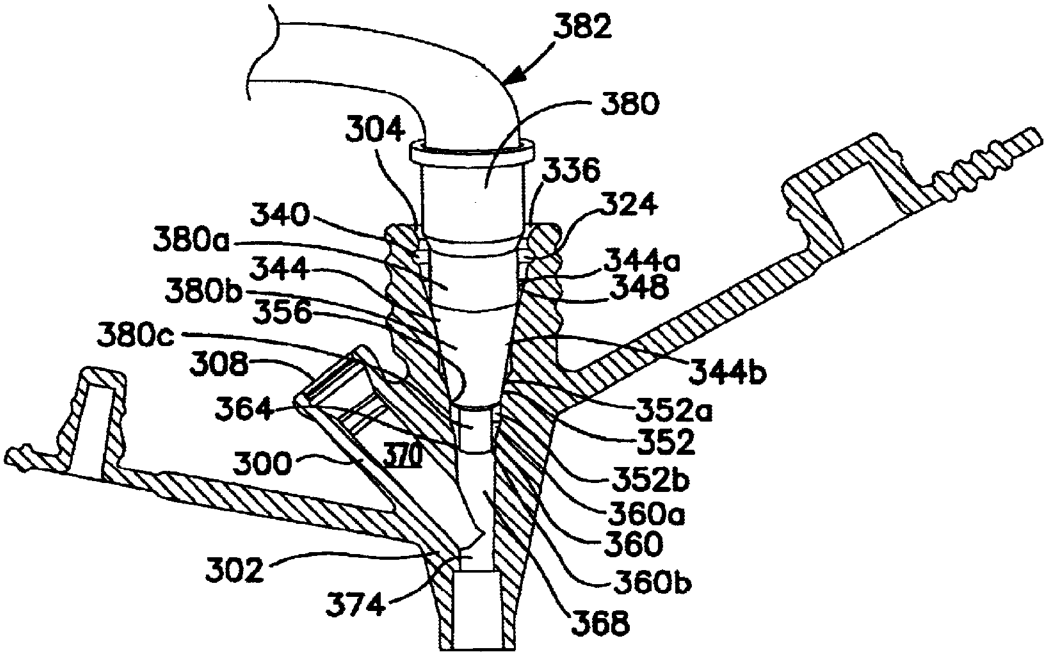
FIG. 8 shows a cross-sectional view of the enteral feeding adapter body of FIG. 7 with the distal end of an infusion set disposed therein.

FIG. 8 shows the adapter body 302 of FIG. 7 mated with the distal end 380 of an infusion set 382. Because the outer diameter of the middle conical step 380*b* of the distal end 380 is varied, the distal end is advanced through the first proximal section 340 and the middle step frictionally engages a significant portion of the arcuate sidewall 348 of the second proximal section 344. The engagement of the middle step 380*b* with the first arcuate sidewall 348 prevents the upper cylindrical step 308*a* from engaging the same sidewall, and prevents the lower cylindrical step 380*c* from engaging the third arcuate sidewall 364.

Figure 9:
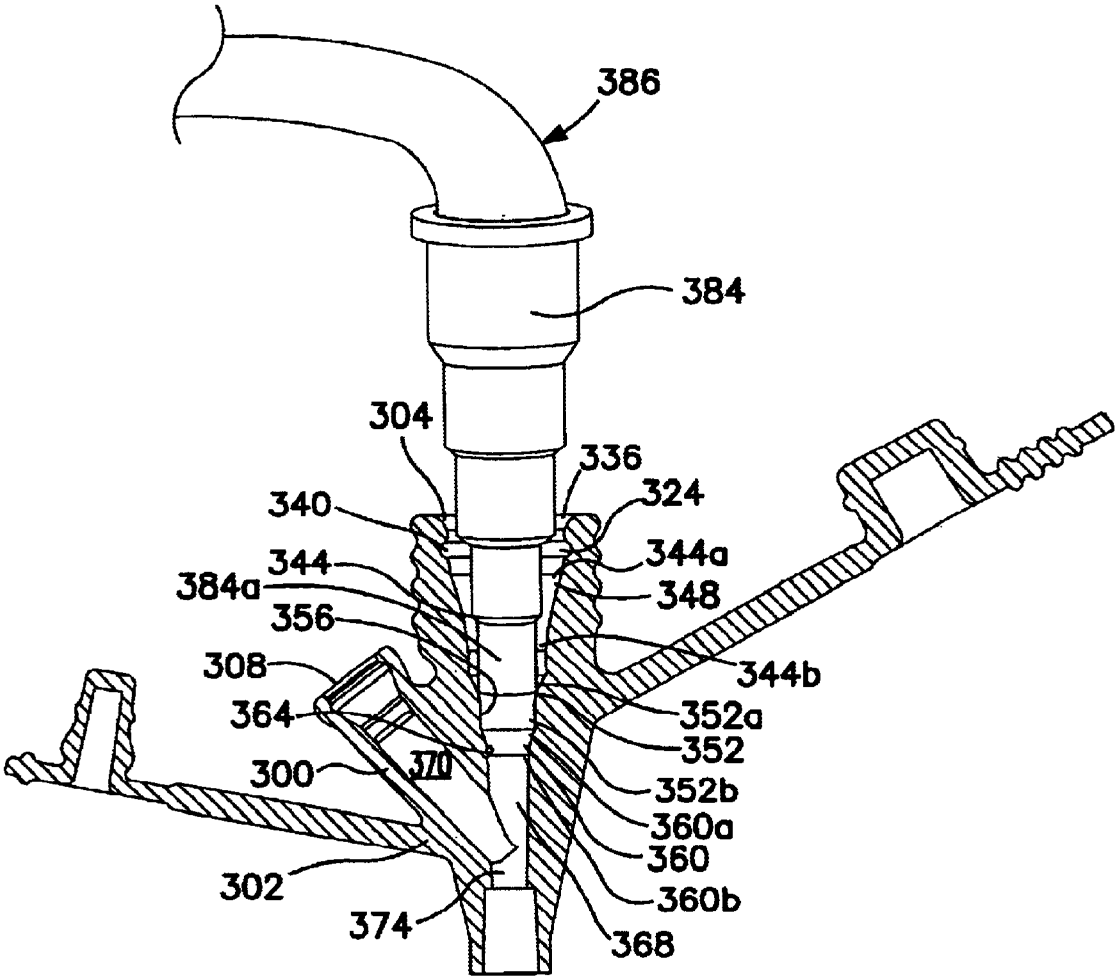
FIG. 9 shows a cross-sectional view of the enteral feeding adapter body of FIG. 7 with the distal end of an infusion set having a different outer diameter than that of FIG. 8.

In contrast, FIG. 9 shows a similar view of the adapter body 302 of FIGS. 7 and 8. However, the outer diameter of distal most step 384*a* of the distal end 384 of the infusion set 386 shown in FIG. 9 is only about 0.24 inches. Thus, the distal end 384 passes through the first proximal section 340 and frictionally engages the arcuate sidewall 356 of the third proximal section 352. The remaining steps of the distal end 384 do not engage the adapter body 302.

Figure 10:
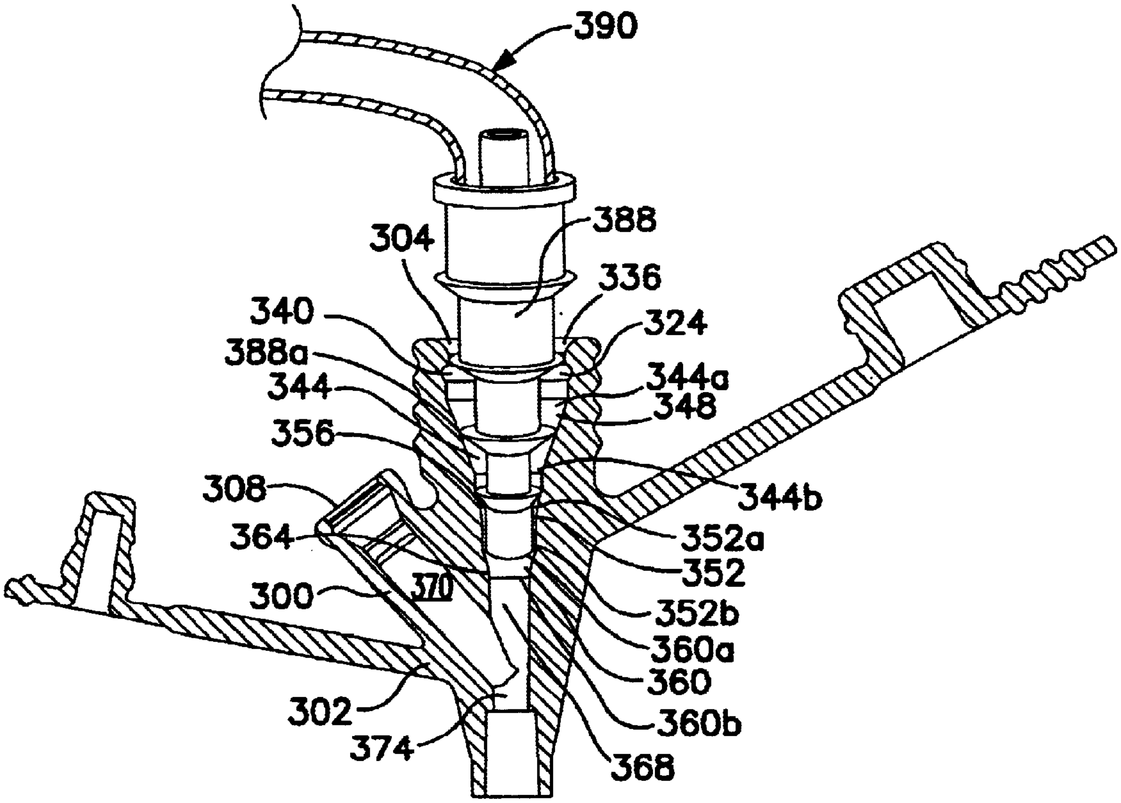
FIG. 10 shows a cross-sectional view of the enteral feeding adapter body of FIG. 7 with the distal end of an infusion set having a different outer diameter than those of FIGS. 8 and 9.

FIG. 10 shows a similar view of the adapter body 302 to that in FIGS. 7 through 9, but includes a distal end 388 of an infusion set 390 which has a step 388*a* with an outer diameter of about 0.28 inches. Because of the size of the step 388*a*, of the distal end 388 and the configuration of the more distal steps, the step 388*a* is the only one which sealingly engages the adapter body 302.

The adapter body 302 shown in FIGS. 7 through 10 provides a marked improvement over the prior art. Rather than receiving the infusion set of a single manufacturer, the adapter body 302 has been demonstrated to securely hold the infusion sets of at least six different manufacturers. Despite the differences in sizes in infusion sets, the adapter body 302 forms an almost universal adapter for connecting infusion sets to gastric balloon catheters. This enables producers of the adapter of the present invention not only to use the adapter with the infusion sets of other manufacturers, it also facilitates the use of gastric balloon catheters and adapters from the same manufacturer. Additionally, clinicians and patients who must change out infusion sets and adapters no longer need to worry about matching the infusion set with the adapter. If the adapter of the present invention is used, the majority of the infusion sets on the market may be used without also requiring changing of the adapter and the gastric balloon catheter.

While industry standards require that a distal end/adapter engagement withstand a pull force of about 4 pounds, use of the adapter shown in FIGS. 7 through 10 has consistently provided a pull resistance of 16 to 20 pounds. Thus, not only does the adapter body 302 enable the use of numerous different infusion sets, it provides a secure engagement of the same which is many times that required in the industry.

Thus, there is disclosed an improved enteral feeding adapter. Those skilled in the art will appreciate numerous modifications which can be made without departing from the scope and spirit of the present invention. The appended claims are intended to cover such modifications.

What is claimed is:

1. An enteral feeding adapter for use in delivering substances into a patient, the enteral feeding adapter suitable for use with a plurality of infusion sets having distal connectors of differing dimensions, the enteral feeding adapter comprising:

an adapter body made of a flexible material containing at least a first port configured for receiving a distal connector of an infusion set, the first port having at least one arcuate sidewall that is deformable for frictionally engaging the distal connector to sealingly secure the distal connector to the adapter body, the at least one arcuate sidewall being deformable such that the area of engagement between the distal connector of the infusion set and the at least one arcuate sidewall is increased, wherein the arcuate sidewall is adapted to assume a compressed configuration when engaging the distal connector to sealingly secure the distal connector to the adapter body, and wherein the arcuate sidewall is adapted to assume an uncompressed configuration after disengaging the distal connector from the arcuate sidewall, the at least one arcuate sidewall that is deformable defining a portion of a passageway through the first port; and a tube extending from the first port for transmitting substances that pass through the first port.

2. The enteral feeding adapter according to claim 1, further comprising a second port configured for injection of medication therethrough into the tube.

3. The enteral feeding adapter according to claim 1, wherein the at least one arcuate sidewall has a radius of curvature between about 0.18 inches and 0.55 inches.

4. The enteral feeding adapter according to claim 3, wherein the radius of curvature of the at least one arcuate sidewall is between about 0.18 inches and 0.22 inches.

5. The enteral feeding adapter according to claim 4, wherein the radius of curvature of the at least one arcuate sidewall is about 0.20 inches.

6. The enteral feeding adapter according to claim 3, wherein the radius of curvature of the least one arcuate sidewall is between about 0.22 and 0.24 inches.

7. The enteral feeding adapter according to claim 6, wherein the radius of curvature of the at least one arcuate sidewall is about 0.23 inches.

8. The enteral feeding adapter according to claim 3, wherein the radius of curvature of the at least one arcuate sidewall is between about 0.45 and 0.55 inches.

9. The enteral feeding adapter according to claim 8, wherein the radius of curvature of the at least one arcuate sidewall is 0.50 inches.

10. The enteral feeding port according to claim 1, wherein the at least one arcuate sidewall defines a proximal portion of the first port, and wherein the first port further includes a second arcuate sidewall.

11. The enteral feeding port according to claim 10, wherein the second arcuate sidewall is disposed distally of the first arcuate sidewall.

12. The enteral feeding port according to claim 10, wherein the first arcuate sidewall has a radius of curvature between about 0.45 and 0.55 inches and wherein the second arcuate sidewall has a radius of curvature between about 0.22 and 0.24 inches.

13. The enteral feeding port according to claim 10, wherein the first port further includes a cylindrical section disposed proximally of the first arcuate sidewall and the second arcuate sidewall.

14. The enteral feeding adapter according to claim 10, wherein the first port further includes a cylindrical portion distal of the first arcuate sidewall and proximal of the second arcuate sidewall.

15. The enteral feeding adapter according to claim 10, wherein the first port further includes a third arcuate sidewall distal of the second arcuate sidewall.

16. The enteral feeding adapter according to claim 15, wherein the first arcuate sidewall has a radius of curvature of between about 0.45 and 0.55 inches, wherein the second arcuate sidewall has a radius of curvature of between about 0.22 and 0.24 inches and wherein the third arcuate sidewall has a radius of curvature of between about 0.18 and 0.22 inches.

17. The enteral feeding adapter according to claim 15, wherein the first arcuate sidewall has a varying diameter between about 0.330 and 0.220 inches, wherein the second arcuate sidewall has a varying diameter between 0.220 and 0.153 inches, and wherein the third arcuate sidewall has a varying diameter between 0.153 and 0.127 inches.

18. An enteral feeding adapter configured for receiving a distal end of an infusion set and for transmitting substances into a patient, the enteral feeding adapter comprising:

an adapter body made of a flexible material having a first port, the first port having at least a cylindrical first section and a second section defined by a first arcuate sidewall disposed distally of the first section, the first arcuate sidewall being deformable to frictionally engage the distal end of the infusion set to secure the distal end of the infusion set to the adapter body, the first arcuate sidewall is deformable such that the area of engagement between the distal end of the infusion set and the first arcuate sidewall is increased, wherein the arcuate sidewall is adapted to assume a compressed configuration when engaging the distal end of the infusion set to secure the distal end of the infusion set to the adapter body, and wherein the arcuate sidewall is adapted to assume an uncompressed configuration after disengaging the distal end of the infusion set from the arcuate sidewall, the first arcuate sidewall defining a portion of a passageway through the first port; and a tube extending from the adapter body for transmitting the substances from the infusion set and thereafter into the patient.

19. The enteral feeding adapter according to claim 18, wherein a diameter of the second section decreases from a proximal end of the second section to a distal end of the second section.

20. The enteral feeding adapter according to claim 18, wherein the first port further includes a third section disposed adjacent to the second section, the third section being defined by a second arcuate sidewall.

21. The enteral feeding adapter according to claim 20, wherein the first section, second section, and third section form a distally extending channel having an increasingly smaller diameter.

22. The enteral feeding adapter according to claim 20, wherein the first port further includes a fourth section disposed adjacent to the third section, the fourth section being defined at least partially by a third arcuate sidewall.

23. The enteral feeding adapter according to claim 22, wherein the first arcuate sidewall has a radius of curvature between about 0.45 and 0.55 inches, wherein the second arcuate sidewall has a radius of curvature between about 0.22 and 0.24 inches, and wherein the third arcuate sidewall has a radius of curvature between about 0.18 and 0.22 inches.

* * * * *